(12) United States Patent
Plihal et al.

(10) Patent No.: US 9,582,869 B2
(45) Date of Patent: Feb. 28, 2017

(54) DYNAMIC BINNING FOR DIVERSIFICATION AND DEFECT DISCOVERY

(71) Applicant: KLA-Tencor Corporation, Milpitas, CA (US)

(72) Inventors: Martin Plihal, Pleasanton, CA (US); Vidyasagar Anantha, Hyderabad (IN)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 14/614,202

(22) Filed: Feb. 4, 2015

(65) Prior Publication Data
US 2016/0110857 A1 Apr. 21, 2016

Related U.S. Application Data

(60) Provisional application No. 62/065,752, filed on Oct. 19, 2014.

(51) Int. Cl.
*G06K 9/00* (2006.01)
*G06T 7/00* (2006.01)
(Continued)

(52) U.S. Cl.
CPC ....... *G06T 7/0004* (2013.01); *G01N 21/8851* (2013.01); *G01N 21/9501* (2013.01); *G01N 21/956* (2013.01); *G06K 9/52* (2013.01); *G06K 9/6255* (2013.01); *G06T 7/001* (2013.01); *G06T 7/004* (2013.01); *G01N 2021/8854* (2013.01);
(Continued)

(58) Field of Classification Search
CPC ... H01L 22/20; H01L 21/67005; H01L 22/12; G06T 2207/30148; G06T 7/0004; G06T 7/0002; G06T 7/001; G06T 7/0006; G06T 5/50; G06T 7/0008; G06T 7/004; G06T 2207/10056; G01N 2021/8854; G01N 21/9501; G01N 21/95607; G01N 21/956; G01N 2021/95676; G01N 21/8851; G01N 2201/12; G01N 21/93; G06F 17/5081; G06F 17/5045; G03F 1/84; G03F 7/7065; G06K 2209/19; G06K 9/52; G06K 9/6256; F04C 2270/0421; G01R 31/318511;
(Continued)

(56) References Cited

U.S. PATENT DOCUMENTS 6,265,232 B1  7/2001  Simmons
6,613,590 B2  9/2003  Simmons
(Continued)

OTHER PUBLICATIONS

International Search Report for PCT/US2015/056169 mailed Dec. 28, 2015.

*Primary Examiner* — Vu Le
*Assistant Examiner* — Aklilu Woldemariam
(74) *Attorney, Agent, or Firm* — Ann Marie Mewherter

(57) ABSTRACT

Methods and systems for generating a defect sample for a wafer are provided. One method includes separating defects detected on a wafer into bins having diversity in values of a first set of one or more first attributes of the defects. The method also includes selecting, independently from one or more of the bins, defects within the bins based on diversity in a second set of one or more second attributes of the defects. The selected defects are then used to create a defect sample for the wafer. In this manner, defects having diverse values of multiple attributes can be easily selected.

37 Claims, 2 Drawing Sheets

(51) Int. Cl.
  *G01N 21/95* (2006.01)
  *G01N 21/956* (2006.01)
  *G06K 9/52* (2006.01)
  *G01N 21/88* (2006.01)
  *G06K 9/62* (2006.01)

(52) U.S. Cl.
  CPC ...... *G06K 9/00* (2013.01); *G06T 2207/30148* (2013.01)

(58) Field of Classification Search
  CPC ...... G01R 31/2894; G05B 2219/37224; Y02P 90/22; H01J 2237/24592
  USPC .......... 382/149, 159, 224, 309; 348/92, 125; 250/306, 307, 310
  See application file for complete search history.

(56) References Cited

U.S. PATENT DOCUMENTS

| | | | |
|---|---|---|---|
| 6,792,367 B2 | 9/2004 | Hosoya et al. | |
| 6,890,775 B2 | 5/2005 | Simmons | |
| 7,739,064 B1 * | 6/2010 | Ryker | G01R 31/2834 700/121 |
| 7,912,276 B2 | 3/2011 | Shibuya et al. | |
| 8,050,488 B2 * | 11/2011 | Kim | G01N 21/95607 348/125 |
| 8,135,204 B1 * | 3/2012 | Chen | G01N 21/9501 250/310 |
| 8,923,600 B2 * | 12/2014 | Zafar | G03F 1/84 382/144 |
| 2005/0071101 A1 * | 3/2005 | Nishimura | H01L 21/67253 702/83 |
| 2005/0158887 A1 | 7/2005 | Simmons | |
| 2006/0082763 A1 | 4/2006 | Teh et al. | |
| 2006/0115143 A1 * | 6/2006 | Auerbach | G01N 21/95607 382/149 |
| 2006/0265145 A1 * | 11/2006 | Huet | G01R 31/2846 702/35 |
| 2006/0287751 A1 | 12/2006 | Dishner et al. | |
| 2007/0133860 A1 * | 6/2007 | Lin | G06T 7/001 382/149 |
| 2007/0156379 A1 * | 7/2007 | Kulkarni | H01L 21/67005 703/14 |
| 2007/0288219 A1 * | 12/2007 | Zafar | G03F 1/84 703/14 |
| 2008/0163140 A1 * | 7/2008 | Fouquet | G03F 1/84 700/110 |
| 2008/0167829 A1 * | 7/2008 | Park | G01N 21/8851 702/81 |
| 2008/0295048 A1 | 11/2008 | Nehmadi et al. | |
| 2012/0027285 A1 | 2/2012 | Shlain et al. | |
| 2014/0050389 A1 * | 2/2014 | Mahadevan | G06T 7/0004 382/149 |
| 2014/0133737 A1 | 5/2014 | Plihal et al. | |
| 2014/0307947 A1 * | 10/2014 | Kurada | G01N 21/95607 382/149 |

* cited by examiner

DYNAMIC BINNING FOR DIVERSIFICATION AND DEFECT DISCOVERY

BACKGROUND OF THE INVENTION

1. Field of the Invention

This invention generally relates to methods and systems for generating a defect sample for a wafer.

2. Description of the Related Art

The following description and examples are not admitted to be prior art by virtue of their inclusion in this section.

One of the most important tasks during setup of wafer inspection recipes is to identify as many defect types as can be detected on a wafer. As automated recipe setup and tuning becomes more important, the need to automatically identify a good set of defects for this optimization becomes increasingly important as well. Without a good training set, automated optimization cannot function well. In addition, during manufacturing ramp up, when high and unknown defectivity is an issue, it is equally important to identify all defects on a wafer. In this situation, the interest is primarily in killer defects.

The need for developing effective sampling algorithms that achieve maximum defect type diversity has been growing with the increasing challenges in optical inspections. As the sizes of defects of interest (DOIs) shrink, optical inspections struggle to maintain differential sensitivity to these defects. To achieve the desired sensitivity, inspections tend to rely less on sophisticated defect detection algorithms and more on complex nuisance filters that leverage the wealth of defect properties (or attributes). However, tuning such filters requires a defect population that is representative of all defect types.

Examples of some methods that are currently used to sample defects from a population are described in U.S. Pat. No. 6,265,232 issued Jul. 24, 2001 to Simmons, U.S. Pat. No. 6,613,590 issued Sep. 2, 2003 to Simmons, U.S. Pat. No. 6,792,367 issued Sep. 14, 2004 to Hosoya et al., U.S. Pat. No. 6,890,775 issued May 10, 2005 to Simmons, and U.S. Pat. No. 7,912,276 issued on Mar. 22, 2011 to Shibuya et al. and U.S. Patent Application Publication Nos. 2005/0158887 published Jul. 21, 2005 to Simmons and 2008/0295048 published on Nov. 27, 2008 to Nehmadi et al., all of which are incorporated by reference as if fully set forth herein.

Accordingly, it would be advantageous to develop systems and/or methods for generating a defect sample for a wafer that can be used for one or more applications described above.

SUMMARY OF THE INVENTION

The following description of various embodiments is not to be construed in any way as limiting the subject matter of the appended claims.

One embodiment relates to a computer-implemented method for generating a defect sample. The method includes acquiring inspection results for the wafer. The inspection results include information for defects detected on the wafer by an inspection process. The information includes information for at least a first set of one or more first attributes for the defects and a second set of one or more second attributes for the defects. The method also includes identifying values of the one or more first attributes having the most diversity in the values of the one or more first attributes. In addition, the method includes generating a set of bins for the defects based on the identified values such that each of the bins corresponds to only a portion of the values and such that the values corresponding to the bins have diversity in the one or more first attributes. The method further includes separating the defects into the bins based on the values of the one or more first attributes corresponding to the defects. The method also includes selecting, from one of the bins, defects within the one of the bins based on diversity in values of the one or more second attributes and repeating the selecting step for at least one other of the bins. In addition, the method includes creating a defect sample for the wafer that includes the defects selected from the one of the bins and the at least one other of the bins. The acquiring, identifying, generating, separating, selecting, repeating, and creating steps are performed by a computer system.

The method described above may be performed as described further herein. In addition, the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for generating a defect sample for a wafer. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to generate a defect sample for a wafer. The system includes an inspection subsystem configured to acquire inspection results for the wafer. The inspection results include the information described above. The system also includes a computer subsystem configured for performing the identifying, generating, separating, selecting, repeating, and creating steps of the method described above. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
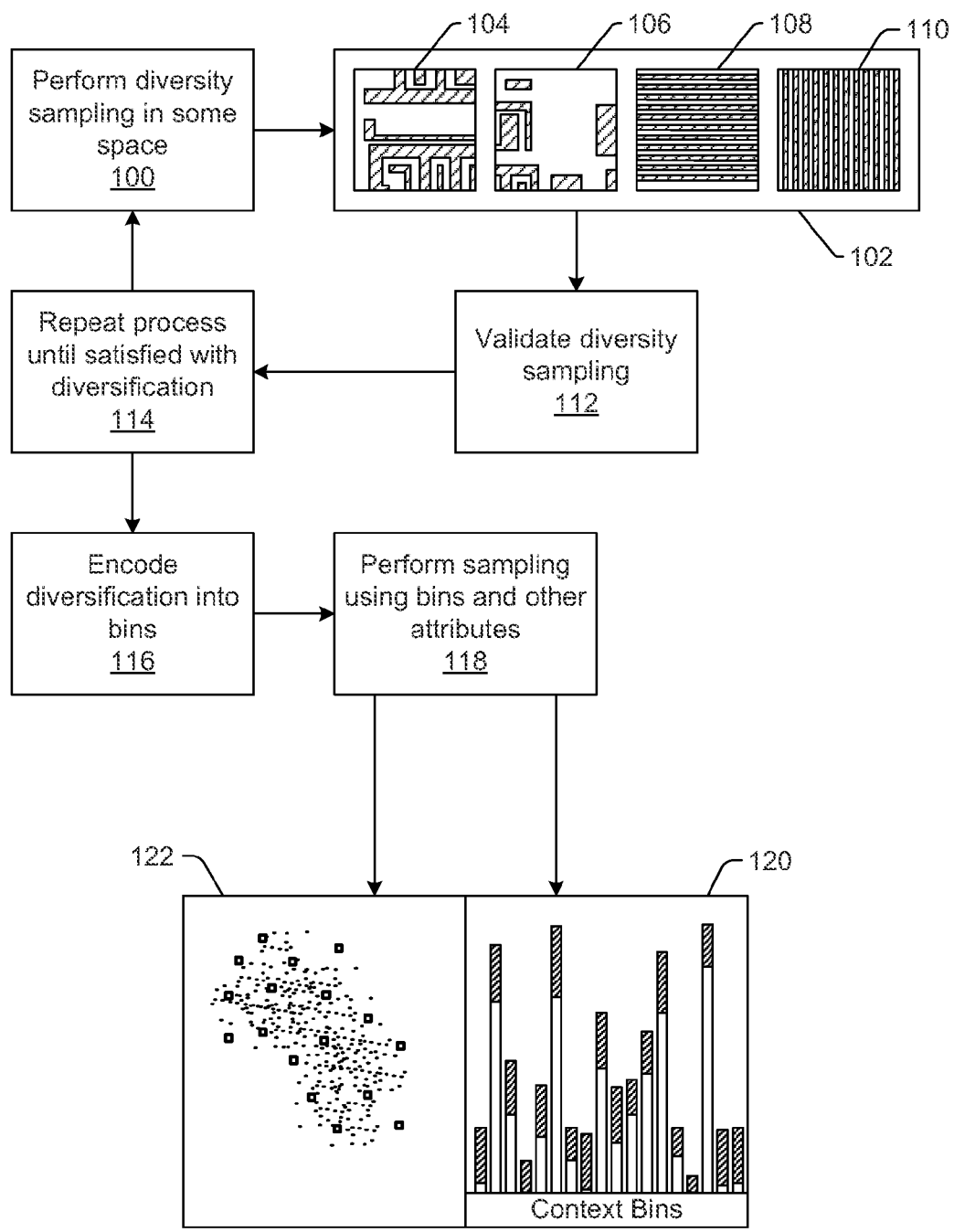
FIG. 1 is a schematic diagram illustrating different steps that may be included in some embodiments of a method for generating a defect sample for a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a computer-implemented method for generating a defect sample for a wafer. In general, the embodiments described herein provide novel diversification methods and systems that can be used in applications such as discovery of defect types. The embodiments described herein fundamentally change the way in which a defect population for optics mode selection or other purposes can be generated. The embodiments described herein can be implemented as offline methods. For example, the embodiments described herein can be implemented in IMPACT, an off-line application designed for classifier tuning, which is commercially available from KLA-Tencor, Milpitas, Calif.

The embodiments described herein provide dynamic binning for improved diversification and defect discovery. Sampling a diverse set of defects is a powerful technique for discovering defect types on a wafer, especially one with a relatively large number of defects. Examples of methods and systems that can be used to generate diversified defect samples are described in U.S. Patent Application Publication No. 2014/0133737 by Plihal et al. published on May 15, 2014, which is incorporated by reference as if fully set forth herein. Some such methods and systems are built on two fundamental principles: user-selectable feature space; and selection of defects that are as far away from each other as possible in this space. For defect discovery, this sampling scheme relies on domain knowledge that can be used effectively to select a relatively small feature space for diversification.

Although the methods and systems described in the above-referenced patent application provide significant advantages over other defect sampling methods and systems, the embodiments described herein provide sampling schemes that improve upon the ones described in that patent application. For example, one potential issue with the approaches described in that patent application is the decreasing ability to diversify a sample effectively as the number of diversification objectives increases (in other words, when the dimensionality of the diversification feature space increases). This can be a problem when the goal is to achieve multiple diversification objectives such as diversification with respect to the context in which the defects find themselves and with respect to the signal attributes. Trying to satisfy these two diverse goals simultaneously dilutes the feature space and makes the sampling scheme less effective in achieving either of the two objectives. The embodiments described herein address this through an intuitive, configurable, and verifiable process. For example, as described further herein, the embodiments provide methods and systems that can achieve multiple diversification objectives much more effectively than current methods and systems. In addition, as described further herein, the embodiments provide a more intuitive, stepwise configuration of the diversification objectives that are more easily verifiable by users.

The method includes acquiring inspection results for a wafer. The inspection results include information for defects detected on the wafer by an inspection process, and the information includes information for at least a first set of one or more first attributes for the defects and a second set of one or more second attributes for the defects. A user may select the inspection results file to be used in the method. The inspection results may include information about the defects detected on the wafer such as the locations of the defects detected on the wafer and any other information for the defects detected on the wafer such as defect attributes determined for the defects and image data or images generated for the defects.

In some embodiments, the one or more first attributes include one or more first attributes of the background or context of the defects. For example, the one or more first attributes may include or more first attributes may include attributes that describe the context around the defects, such as its brightness, texture, etc, or the pattern around the defects. These attributes, or a subset of them, can be used to create the dynamic bins as described further herein that can be used as described further herein to diversify the defects with respect to the context in which the defects are located. The one or more first attributes may also include other non-context related attributes of the defects and/or one or more context-related attributes and one or more non-context related attributes of the defects.

As described above, the first attribute(s) related to the context may be determined from the output of the inspection system for the wafer. In other words, the first attribute(s) may be related to how the context appears in the output of the inspection system. However, the first attribute(s) that are related to the context may be also be determined from other sources such as the design data for the wafer. For example, some context-related attributes that can be used as the first attribute(s) include design-based attributes such as pattern density, etc. that can be used to characterize the context.

Furthermore, the first attribute(s) may include one or more attributes that characterize the pixels right around the defect and its optical response characteristics, but not the defect signal itself. Therefore, such attributes may be related to a much smaller context than the context-related attributes described above. Examples of such attributes include the gray level determined by a defect detection algorithm such as the multi-die automatic thresholding (MDAT) algorithm used by some inspection systems that are commercially available from KLA-Tencor, Milpitas, Calif. (e.g., "MDAT_GL"), roughness of a reference image used to detect the defect ("REFERENCE_Roughness"), brightness of a reference image used to detect the defect (REFERENCE_Brightness"), and polarity (e.g., whether the defect signal is bright or dark compared to the surrounding signals).

In an additional embodiment, the one or more second attributes include one or more attributes of a signal detected for the defects. For instance, the one or more second attributes may include optical signal attributes such as energy, magnitude, etc. Additional examples of the second attribute(s) include an energy parameter determined by a defect detection algorithm ("Energy_Param") and other parameters determined by defect detection algorithms (e.g., "IMX_Param3," "IMX_Param5," and "SpotLikeness"). The one or more second attributes may also include other non-signal related attributes of the defects and/or one or more signal-related attributes and one or more non-signal related attributes of the defects.

The first attribute(s) and the second attribute(s) can also vary depending on the diversification criteria to be used in the embodiments described herein, which may vary depending on the use case, wafer, process step, etc. For example, additional examples of first and/or second attribute(s) include defect position with respect to care edge, defect position in a die, distance between defect and wafer edge, etc. In addition, the embodiments described herein are not limited to the first and second attribute(s) described herein. In other words, the embodiments described herein can be configured to use any first and second attributes that can be determined for wafer defects.

The method also includes identifying values of the one or more first attributes having the most diversity in the values of the one or more first attributes. The one or more first attributes may be selected for use in the embodiments described herein as described further herein. Identifying the values having the most diversity for the first attribute(s) may be performed in a variety of ways depending on the first attribute(s). In addition, since, as described further herein, the diverse values of the first attribute(s) will be used to define bins for the defects, the diversity in the values of the first attribute(s) may be determined based on the number of bins selected for use in the method. For example, if the number of bins selected for use in the method is 10, then the 10 values of the first attribute(s) having the most diversity may be identified. In some instances in which the values of one of the first attribute(s) are discrete "values" (as opposed to a continuous range of values for the one of the first attribute(s)), the values that are identified as having the most diversity may be the values that are most different from each other. Such diversity may also be defined for "values" that are difficult to define numerically such as when one of the first attribute(s) is related to the context of a defect (or patterned features at or near a defect location). Therefore, the "values" of the first attribute(s) are not limited to numerical values but instead may be qualitative type values. In instances in which the values of one of the first attribute(s) are within a continuous range of values, the total range may be divided by the number of bins to be used in the method to produce different, non-overlapping subsets of the values within the entire range.

In one embodiment, the first attribute(s) and a number of the bins included in the set generated as described further herein are selected by a user. The concept of diversification bins described herein is powerful because the number of bins itself can be used to change the balance between diversification goals and priorities. Larger numbers of bins created from a given feature sub-space will force the final sampling scheme to be more strict about the diversification in this space, whereas fewer bins will have the opposite effect. In some embodiments, the method may include requesting the first attribute(s) and the number of the bins from a user. Steps of the method may then be performed when the information has been received. In some such instances, the method may include displaying all of the defect attributes that are included in the inspection results to a user and requesting the user to select one or all of the defect attributes for use as the first attribute(s).

The method further includes generating a set of bins for the defects based on the identified values such that each of the bins corresponds to only a portion of the values and such that the values corresponding to the bins have diversity (e.g., the most diversity) in the first attribute(s). In other words, the bins to be used in the method may be defined based on the identified values such that each of the bins corresponds to only one of the identified values. Therefore, the embodiments described herein utilize a concept of dynamic binning that is achieved through a diversification process in one feature space with a specific diversification in mind. In some embodiments, generating the set of bins includes sampling at least one of the defects having each of the identified values from the inspection results and defining the bins based on the sampled at least one of the defects having each of the identified values. For example, the diversification can be accomplished by sampling a diverse set of defects in the first attribute space(s) and creating nearest neighbor bins with the sampled defects as seeds. The bin creation described above may be integrated into diversity sampling itself, or it can be performed separately and independently of sampling.

In some such embodiments, as shown in FIG. 1, the method may include performing diversity sampling in some space, as shown in step 100. This step may be performed to get diverse values of the first attribute(s) such as diverse context. For example, diverse sampling in context space (where context of a defect is defined by the patterned features at and/or near the defect location) may produce a set of diverse contexts, shown in FIG. 1 as set 102 of contexts 104, 106, 108, and 110 that are each substantially different from each other and therefore are diverse. It is noted that the contexts shown in FIG. 1 are meant only to further understanding of the invention and are not intended to show any actual context that may be formed on any actual wafer. In addition, it is noted that no defects are shown in these contexts since the embodiments described herein can be used for any defects that can be detected on a wafer. Furthermore, the contexts shown in FIG. 1 are shown as they might appear in a design for a wafer, but the contexts that are used in the method may be determined from images of wafer defects and may therefore appear not as they would in a design but as they would in images of a wafer produced by wafer inspection. Moreover, although the set of contexts is shown in FIG. 1 as including 4 different contexts, clearly the number of different contexts included in the set may vary depending on the number of bins, which may be selected by a user.

The embodiment shown in FIG. 1 includes validating the diversity sampling, as shown in step 112. Validating the diversity sampling may include displaying the diverse values of the first attribute(s) such as the diverse contexts shown in FIG. 1 to a user and requesting from the user a validation of the diversity sampling. In this manner, validating the diversity sampling may be performed, at least in part, visually by a user. Validating the diversity sampling may also include validating that the sampled defects produce a diverse set of the first attribute(s) such as substantially different contexts and validating that values of the first attribute(s) that are relatively close to each other are substantially similar to each other. Such validating may also be performed by a user. Upon receiving input from a user as to the validation of the diversity sampling results with respect to the first defect attribute(s), the method may include a number of steps such as modifying the diversity sampling or performing other steps described herein.

The method includes separating the defects into the bins based on the values of the first attribute(s) corresponding to the defects. For example, once the bins have been generated as described above with the sampled defects having the identified values of the first attribute(s) as seeds, those sampled defects can be used to separate the remaining defects into the bins based on the nearest neighbor concept.

In another embodiment, the method and the generating step do not include tuning cutlines separating the bins from each other. Therefore, the way that the bins described herein are created/trained is believed to be new. In particular, instead of performing cutline tuning during creation of the bins, creating the bins may just be based on user-defined feature selection, with the choice of sample size determining binning, and the quality of the bins may be determined by validating diversity visually through patch inspection, scatter plot distributions, etc., which may be performed as described further herein.

In some embodiments, the method includes determining one or more characteristics of the bins based on the defects separated into the bins, displaying the one or more characteristics to a user prior to the selecting step described further herein, and requesting from the user a validation of the one or more characteristics. In this manner, the method may include validating the separation of the defects into bins. Validating the defect binning may include displaying the binning results to a user and requesting from the user a validation of the binning. In this manner, validating the diversity sampling may be performed visually. Validating the defect separation into bins may also include validating that defects within a bin created with the sampled defects do not vary much. As shown in step 114 of FIG. 1, the method may also include repeating the above-described process until satisfied with diversification. In other words, determining diverse values of the first attribute(s), generating the bins, and separating the defects into the bins may be performed repeatedly until a user validates the results of the binning and/or the method determines that the binning results meet some predetermined criteria, which may also be set in advance by a user. As further shown in step 116 of FIG. 1, the method may include encoding the diversification into bins. For example, when the desired diversification is obtained, the diversification may be encoded into bins centered on the sampled defects (i.e., nearest neighbor bins defined by the sampled defects).

The method also includes selecting, from one of the bins, defects within the one of the bins based on diversity in values of the one or more second attributes and repeating the selecting step for at least one other of the bins. In some embodiments, the selecting step is performed based on the diversity such that the defects selected from the one of the bins have the most diversity in the values of the one or more second attributes. In this manner, diversification with respect to discrete features (e.g., bins or groups) is defined in terms of the sample distribution across the discrete values instead of a distance measure. In other words, the newly created bins may be used as a defect feature in the final diversification sampling. For example, as shown in step 118 of FIG. 1, the method may include performing sampling using bins and other attributes. This step may include using the bins created as described above along with the "other" attribute(s) as described herein to configure the desired sampling strategy and to perform sampling. The best diversification in a discrete attribute (such as the discrete values of the first attribute(s) corresponding to each of the bins) is achieved by sampling roughly the same number of defects from each discrete value. As such, in some embodiments, the same number of defects are selected from each of the bins from which defects are selected. In contrast, the best diversification in a continuous attribute is achieved by sampling defects as far from each other as possible (i.e., based on distance).

The embodiments described herein, therefore, are based on generating diversification bins in a smaller sub-space of the feature space to achieve a certain type of diversification, and then using those bins to achieve efficient simultaneous diversification in a different sub-space. The embodiments can also diversify the defects with respect to additional attribute(s) as described further herein. The individual diversification strategies can, therefore, be combined into a single diversification process through the embodiments described herein (e.g., through the user-configurable process described herein and by combining newly created bins with other features). The second diversification will use entirely different feature space from the first diversification, but both objectives will be achieved through the use of the bin attribute as one of the features in the second diversification. As such, the embodiments described herein can achieve multiple diversification objectives much more effectively than the current methods and systems and provide a more intuitive, stepwise configuration of the diversification objectives. Therefore, an advantage of the embodiments described herein is that this method provides an intuitive way of partitioning the diversification process into intuitive, controlled, and verifiable steps. These steps can be combined into a comprehensive diversification strategy that achieves all the partial objectives simultaneously and rather well. The embodiments described herein also provide a substantially efficient dimensionality reduction that increases the diversification efficiency especially for relatively small samples. In addition, the embodiments described herein introduce a new dimensionality reduction technique for defect sample diversification in relatively high dimensional feature spaces. Furthermore, the embodiments described herein provide unprecedented flexibility in implementing relatively complex sampling strategies.

In another embodiment, the selecting step is performed independently for each of the bins from which defects are selected. For example, each of the sub-populations into which the defects have been binned may be considered separately from each of the other sub-populations of defects. In this manner, the diversity of the defects with respect to the second attribute(s) may be considered separately for each sub-population. As such, separate and independent diversification can be achieved automatically by combining the discrete bin attribute with the second diversification space. For example, roughly the same sample can be selected from each bin, which in turn makes the diversification with respect to the second attribute(s) essentially an independent process for each bin. Separately selecting the defects from each of the bins for diversity in the second attribute(s) may be important since the diversity of the defects in the second attribute(s) may vary from bin-to-bin. For example, in the case of the first attribute(s) being related to the defect context and the second attribute(s) being related to the defect signal, defects in one context may exhibit different diversity in defect signal compared to the defects in another context.

In another embodiment, the selecting step is performed based on the diversity and one or more sample biasing parameters. The one or more sample biasing parameters may be received from a user of the embodiments described herein. For example, if a user has prior knowledge about the types of defects that may be present on the wafer and that may be of particular interest, the user can set the biasing parameters based on anticipated attribute(s) of those types of defects such that those defects are selected more heavily for inclusion in the defect sample than other types of defects. In one such example, if a user knows that a defect type of particular interest should have a particular polarity in its defect signal, the biasing parameter(s) can be set to select defects having that polarity more heavily from the bins than defects having the opposite polarity. The biasing parameter(s) may be incorporated into the method and/or algorithm used for the selecting step in any suitable manner. In this manner, the embodiments described herein may be configured to create diverse samples that are also biased towards some particular type of defects.

In a further embodiment, the method includes storing information for the bins into which the defects are separated as a bin attribute for each of the defects that is separated into a bin, and the selecting and repeating steps described above are performed based on the bin attributes of the defects. For example, the embodiments described herein may have setup and execution capabilities to introduce the ability to save the sampling results in the form of new defect (bin) attributes that can be later added to the diversification features in the final defect sampling. In addition, the created bins (or bin attributes) can be saved into a lot result (i.e., the inspection results data file) as new defect features or a source of useful information, or they could be transient features or attributes only used for the sampling. The embodiments described herein may also have setup and execution capabilities to construct a sequencer of the various pre-configured sampling schemes to produce the necessary data (bins) and to execute the final sample.

In one embodiment, the first attribute(s) include one or more attributes of background of the defects on the wafer (where the background is the pattern behind the defect visible in the defect patch image). In another embodiment, the second attribute(s) include one or more characteristics of a signal detected for the defects in the inspection process. For example, as described further herein, users can diversify a defect population based on the image patch background, verify the effectiveness of the diversification by inspecting patches of the sampled defects, and then lock the diversification into bins when they are happy. In the second step, they can use the bins to maintain diversification with respect to background and add diversification with respect to the defect (signal) attribute(s), etc. In this manner, users can diversify with respect to the defect context (encoded into the newly created bins) and then sample relatively large energy defects from each of the contexts.

In one embodiment, the method includes determining one or more characteristics of the defects selected from the bins, displaying the one or more characteristics to a user prior to the creating step described further herein, and requesting from the user a validation of the one or more characteristics. The one or more characteristics of the defects selected from the bins may be determined as described further herein and may be displayed as described further herein. In addition, requesting from the user a validation of these one or more characteristics may be performed as described further herein. In this manner, the diversification with respect to at least some (or each of the) attributes may be validated before the defect sample is created.

In some embodiments, the method includes determining a first characteristic of the bins based on the defects separated into the bins, the method also includes determining a second characteristic of the defects selected from the bins, the first characteristic is not the same as the second characteristic, and the method further includes displaying the first and second characteristics to a user prior to the creating step described further herein and requesting from the user a validation of the first and second characteristics. In other words, depending on the attribute(s) being used for diversification, the results of binning or sampling may be displayed to a user. As such, different characteristics of the results of the steps described herein may be displayed to a user for verification based on the attribute(s) used in the steps. For example, some diversification can be verified by looking at image patches, while other diversification may require validation through scatter plots, etc. In any case, being able to display the results to a user based on the attribute(s) used for diversification can make the results more easily verifiable by users.

In one such example shown in FIG. 1 in which the first attribute(s) are related to context and the second attribute(s) are related to defect signal, sampling results 120 and 122 may be displayed to a user. As can be seen in these sampling results, dramatically different information is conveyed to a user in dramatically different ways. For example, results 120 are an example of the results that may be displayed when the first attribute(s) used to create the bins are related to context. In this display, a pareto is generated and displayed by the method showing the number of defects separated into different context-related bins as well as the number of defects that are sampled from each bin (the portions of the bars containing a pattern represent the portion of defects that is sampled from each bin and the portions of the bars that do not contain a pattern show the portion of defects that is not sampled from each bin). Although the different portions of the defects sampled from at least some of the different context-related bins are shown to be different in FIG. 1 (i.e., not the same from context-related bin to context-related bin), the same portion or number of defects may be selected from each of the context-related bins (unless the number of defects included in any one context-related bin is less than the number of defects being selected from each bin, in which case, all of the defects included in the bin may be selected). In this manner, the user can easily determine from the displayed results if all bins have been sampled thoroughly and if all contexts are represented in the sample.

Results 122 are an example of the results that may be displayed when the second attribute(s) used to create the bins are related to defect signal. In this display, a scatter plot is generated and displayed by the method showing the second attribute(s) of the defect signals of the defects detected on the wafer as well as the second attribute(s) of the defect signals of the defects that were detected on the wafer and sampled from the entire population of defects. In particular, the solid dots shown in the plot represent defects that are included in the population and were not sampled while the open squares in the plot show the defects that are included in the same population and were sampled. Therefore, the user can easily determine from these displayed results if the "other" space of the defect attribute(s) is also sampled thoroughly. As such, by displaying different results to a user, the user can determine if both (or all) of the diversification objectives have been achieved. As described herein, therefore, the embodiments may rely on human input and validation to configure the multiplicity of diversification objectives. In addition, the results of the steps described herein that are displayed to a user for validation may include results other than those shown in FIG. 1 based on the attribute(s) used in the method.

The method also includes creating a defect sample for the wafer that includes the defects selected from the one of the bins and the at least one other of the bins. In other words, the information for all of the defects sampled from all of the bins may be combined together into a single file thereby creating a defect sample. The created defect sample may be output as an inspection results file that can be used by any other method or system or can be used by the methods and systems described herein. The inspection results file that includes the created defect sample may also include any information generated for the created defect sample by the embodiments described herein possibly in combination with any other information from the original inspection results file including any of that used by the embodiments described herein.

Although some embodiments are described herein with respect to two sets of defect attributes, the number of diversification objectives can be larger than two. In the case of multiple diversification goals, multiple sets of bin attributes can be created, one for each diversification objective, and used in the final sampling scheme. Some such embodiments are described further below. However, we only characterized two-step diversification experimentally, and that is where we see significant improvement in the overall diversification.

In some embodiments, the method includes separately selecting, from the one of the bins, defects within the one of the bins based on diversity in values of one or more third attributes of the defects, the method also includes repeating the separately selecting step for the at least one other of the bins, and creating the defect sample includes adding the defects separately selected from the one of the bins and the at least one other of the bins to the defect sample. In this manner, the same bins that were created based on diversity in the first attribute(s) may be used for diversifying with respect to third attribute(s). In other words, the bins may be sampled once for diversity in second attribute(s) and then again for diversity in third attribute(s). A defect sample including the defects sampled in this manner may be created as described further herein. Each of these steps may be performed as described further herein.

In another embodiment, the method includes generating a set of sub-bins for a bin from which the defects were selected based on the values of the second attribute(s) such that each of the sub-bins corresponds to only a portion of the values of the second attribute(s) and such that the values of the second attribute(s) corresponding to the sub-bins have diversity in the second attribute(s). In this manner, after the bins that are created based on diversity in the first attribute(s) are sampled to diversify with respect to the second attribute(s), different sub-bins can be generated (in the same manner that the bins are generated as described herein) that are then diversified with respect to the first attribute(s) and the second attribute(s). Those sub-bins can then be sampled for diversity in third attribute(s). For example, in one such embodiment, the method includes separately selecting, from one of the sub-bins, defects within the one of the sub-bins based on diversity in values of third attribute(s) of the defects, the method also includes repeating the separately selecting for at least one other of the sub-bins, and creating the defect sample includes adding the defects separately selected from the one of the sub-bins and the at least one other of the sub-bins to the defect sample. Each of these steps may be performed as described further herein. In this manner, the resulting defect sample can be diversified with respect to more than two sets of attributes.

In some embodiments, the method is performed for one or more other wafers, and the set of bins generated for the wafer is not used as a set of bins for the one or more other wafers. For example, the embodiments described herein are not necessarily intended to be used to set up a defect sampling strategy using one wafer and then applying that set strategy for other wafers of the same type. In particular, a primary objective for the embodiments described herein is to provide a new method for diversifying samples, especially when there are many diversification objectives, as well as providing a flexible way of enabling many different (as well as possibly complex) sampling strategies. However, the sampling scheme described herein could be set up on one wafer (including setting up the bins), and the same setup can be used on other wafers. In this case, the bins described herein may be created dynamically on each wafer, i.e., the boundaries between the bins may be in different locations on each wafer. In other words, the number of bins may be specified by a user, but the boundaries between the bins may move around with defect distribution on a wafer-to-wafer basis.

The acquiring, identifying, generating, separating, selecting, repeating, and creating steps described above are performed by a computer system, which may be configured as described herein.

In one embodiment, the method includes setting up an inspection recipe based on the defect sample. In this manner, the embodiments described herein can identify a relatively small, but substantially diverse, sample of defects to be used for automatic or manual recipe set up or optimization. Setting up the inspection recipe using the defect sample may be performed in any suitable manner known in the art and may include selecting one or more hardware parameters (e.g., optical parameter(s) such as illumination wavelength and/or angle of incidence) and/or one or more software parameters (e.g., defect detection parameters such as threshold of a defect detection algorithm). For example, the defect sample, including the much more diversified set of defects, may be sent to a defect review tool and used with the wafer to classify one or more of the sampled defects. In this manner, the user may classify one or more of the defects in the created sample and use the classified defects along with the wafer for recipe optimization.

In some embodiments, the wafer has unknown defectivity. For example, the embodiments described herein can identify a relatively small, but substantially diverse, sample of defects to be used for engineering analysis during device ramp up. In addition, the embodiments described herein can reduce the time-to-DOI and improve DOI sampling on unknown layers and devices. Furthermore, the unknown defectivity may not be just unknown locations and numbers of known defect types of interest on a wafer, but unknown defect types of interest. For example, as described above, the wafer may be fabricated during device ramp up of an unknown layer and device. Therefore, any information about what kinds of defects may be present on the wafer and characteristics of any defects that may be present on the wafer may be unknown. Such information can, however, be acquired using a defect sample created as described herein.

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figure 2:
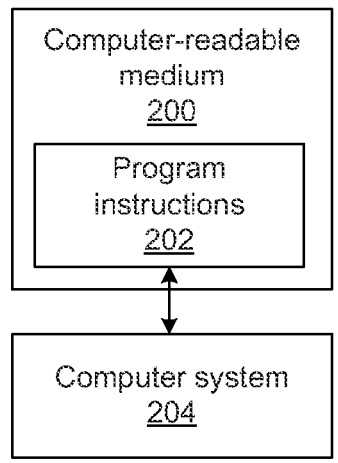
FIG. 2 is a block diagram illustrating one embodiment of a non-transitory computer-readable medium storing program instructions executable on a computer system for performing one or more of the computer-implemented methods described herein.

An additional embodiment relates to a non-transitory computer-readable medium storing program instructions executable on a computer system for performing a computer-implemented method for generating a defect sample for a wafer. One such embodiment is shown in FIG. 2. In particular, as shown in FIG. 2, computer-readable medium 200 includes program instructions 202 executable on computer system 204. The computer-implemented method includes the steps of the method described above. The computer-implemented method for which the program instructions are executable may include any other step(s) described herein.

Program instructions 202 implementing methods such as those described herein may be stored on computer-readable medium 200. The computer-readable medium may be a storage medium such as a magnetic or optical disk, or a magnetic tape or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 3:
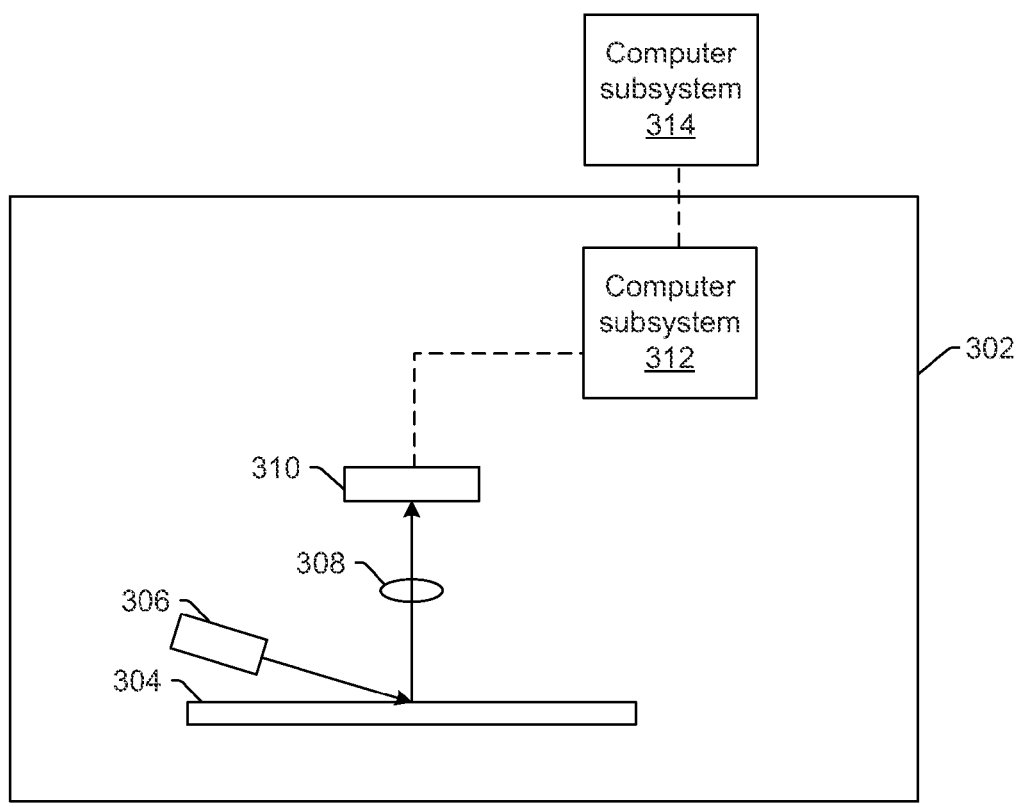
FIG. 3 is a schematic diagram illustrating a side view of one embodiment of a system configured to generate a defect sample for a wafer.

An additional embodiment relates to a system configured to generate a defect sample for a wafer. One embodiment of such a system is shown in FIG. 3. The system includes inspection subsystem 302 configured to acquire inspection results for wafer 304. The inspection results include information for defects detected on the wafer by an inspection process, and the information includes information for at least a first set of one or more first attributes for the defects and a second set of one or more second attributes for the defects. The inspection results may include any such information described herein.

The inspection subsystem includes source 306 that may include any suitable light source in the case of an optical or light-based inspection subsystem. Although the inspection subsystem will be described further herein with respect to a light-based inspection subsystem, the inspection subsystem may be modified in any suitable manner or replaced to make it an electron beam-based inspection subsystem.

Light from the light source may be directed to wafer 304. The light source may be coupled to any other suitable elements (not shown) such as one or more condensing lenses, collimating lenses, relay lenses, objective lenses, apertures, spectral filters, polarizing components and the like. As shown in FIG. 3, the light may be directed to the wafer at an oblique angle of incidence. However, the light may be directed to the wafer at any suitable angle of incidence including near normal and normal incidence. In addition, the light or multiple light beams may be directed to the wafer at more than one angle of incidence sequentially or simultaneously.

Wafer 304 may disposed upon a stage (not shown) while the light is being directed to the wafer. The stage may include any suitable mechanical or robotic assembly and may be configured to move the wafer in one or more directions while the light is being directed to the wafer such that the light can be scanned over the wafer by the inspection subsystem. However, the inspection subsystem may be configured to scan the light over the wafer in any other suitable manner.

The inspection subsystem also includes collector 308 configured to collect light scattered from the wafer (in the case of a dark field capable inspection system), which is configured to direct the collected light to detector 310 that is configured to detect the light scattered from the wafer that is collected by the collector. The collector may include any suitable number and configuration of reflective and/or refractive optical elements. Detector 310 may include any suitable detector. Detector 310 and collector 308 may therefore form at least a portion of a detection subsystem of the inspection subsystem. The detection subsystem may include one or more other suitable elements (not shown) positioned in the optical path between the detector and the wafer such as objective lenses, relay lenses, magnification lenses, zooming lenses, apertures, spectral filters, gratings, and polarizing components. Although the inspection subsystem is shown in FIG. 3 to detect light scattered from the wafer, the inspection subsystem may also or alternatively be configured for bright field (BF) inspection of the wafer. The inspection subsystem may also include more than one detector (not shown), which may be used to detect different light from the wafer simultaneously or sequentially.

The inspection subsystem may include computer subsystem 312 configured to generate the inspection results described herein. For example, computer subsystem 312 may be coupled to detector 310 by one or more transmission media (not shown), which may include "wired" and/or "wireless" transmission media such that the computer subsystem can receive the output of the detector. The computer subsystem may then use the output to detect defects on the wafer as described herein and to determine any of multiple attributes of the defects. Information generated by computer subsystem 312 may then be output by the computer subsystem in the form of an inspection results file as described further herein.

The inspection subsystem may include one computer subsystem that is configured to detect the defects on the wafer, and the system may include another, different computer subsystem that is configured to perform the steps of the methods described herein. For example, the system may include computer subsystem 314 that may be coupled to computer subsystem 312 as described above such that computer subsystem 314 can receive the inspection results from computer subsystem 312. Computer subsystem 314 is configured for performing the identifying, generating, separating, selecting, repeating, and creating steps described herein, which may be performed as described herein. The computer subsystem and the system may be configured to perform any other step(s) described herein and may be further configured as described herein. In addition, the system may include only one computer subsystem (e.g., only computer subsystem 312) that is configured to perform all of the step(s) described herein. This may be the case when an inspection tool is configured to perform the method embodiments described herein. For example, the inspection subsystem shown in FIG. 3 may be configured as an inspection tool that both detects defects on the wafer and creates a defect sample as described herein.

It is noted that FIG. 3 is provided herein to generally illustrate one configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection system (e.g., by adding functionality described herein to an existing inspection system) such as the Puma 90xx, 91xx, and 93xx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Further modifications and alternative embodiments of various aspects of the invention will be apparent to those skilled in the art in view of this description. For example, methods and systems for generating a defect sample for a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for generating a defect sample for a wafer, comprising:

acquiring inspection results for the wafer, wherein the inspection results comprise information for defects detected on the wafer by an inspection process, and wherein the information comprises information for at least a first set of one or more first attributes for the defects and a second set of one or more second attributes for the defects;

identifying values of the one or more first attributes having the most diversity in the values of the one or more first attributes;

generating a set of bins for the defects based on the identified values such that each of the bins corresponds to only a portion of the values and such that the values corresponding to the bins have diversity in the one or more first attributes, wherein generating the set of bins does not include sampling any of the defects, wherein diversification of the set of bins in the one or more first attributes is controlled by a number of the bins in the set, and wherein the number of the bins in the set is received from a user prior to the generating step;

separating the defects into the bins based on the values of the one or more first attributes corresponding to the defects, wherein separating the defects into the bins is not performed until after the set of bins have been generated;

selecting, from one of the bins, defects within the one of the bins based on diversity in values of the one or more second attributes;

repeating said selecting for at least one of the bins; and creating a defect sample for the wafer comprising the defects selected from the one of the bins and the at least one other of the bins, wherein said acquiring, said identifying, said generating, said separating, said selecting, said repeating, and said creating are performed by a computer system.

2. The method of claim 1, wherein the one or more first attributes comprise one or more attributes of background of the defects on the wafer.

3. The method of claim 1, wherein the one or more second attributes comprise one or more characteristics of a signal detected for the defects in the inspection process.

4. The method of claim 1, wherein the wafer has unknown defectivity.

5. The method of claim 1, wherein the one or more first attributes are selected by a user.

6. The method of claim 1, further comprising determining one or more characteristics of the bins based on the defects separated into the bins, displaying the one or more characteristics to a user prior to said selecting, and requesting from the user a validation of the one or more characteristics.

7. The method of claim 1, further comprising determining one or more characteristics of the defects selected from the bins, displaying the one or more characteristics to a user prior to said creating, and requesting from the user a validation of the one or more characteristics.

8. The method of claim 1, further comprising determining a first characteristic of the bins based on the defects separated into the bins, determining a second characteristic of the defects selected from the bins, wherein the first characteristic is not the same as the second characteristic, displaying the first and second characteristics to a user prior to said creating, and requesting from the user a validation of the first and second characteristics.

9. The method of claim 1, wherein said selecting is performed based on the diversity such that the defects selected from the one of the bins have the most diversity in the values of the one or more second attributes.

10. The method of claim 1, wherein said selecting is performed based on the diversity and one or more sample biasing parameters.

11. The method of claim 1, further comprising separately selecting, from the one of the bins, defects within the one of the bins based on diversity in values of one or more third attributes of the defects, further comprising repeating said separately selecting for the at least one other of the bins, and wherein creating the detect sample comprises adding the defects separately selected from the one of the bins and the at least one other of the bins to the defect sample.

12. The method of claim 1, further comprising generating a set of sub-bins for a bin from which the defects were selected based on the values of the one or more second attributes such that each of the sub-bins corresponds to only a portion of the values of the one or more second attributes and such that the values of the one or more second attributes corresponding to the sub-bins have diversity in the one or more second attributes.

13. The method of claim 12, further comprising separately selecting, from one of the sub-bins, defects within the one of the sub-bins based on diversity in values of one or more third attributes of the defects, further comprising repeating said separately selecting for at least one other of the sub-bins, and wherein creating the defect sample comprises adding the defects separately selected from the one of the sub-bins and the at least one other of the sub-bins to the defect sample.

14. The method of claim 1, wherein the same number of defects are selected from each of the bins from which defects are selected.

15. The method of claim 1, wherein said selecting is performed independently for each of the bins from which defects are selected.

16. The method of claim 1, further comprising storing information for the bins into which the defects are separated as a bin attribute for each of the defects that is separated into a bin, wherein said selecting and said repeating are performed based on the bin attributes of the defects.

17. The method of claim 1, wherein the method and said generating do not comprise tuning cutlines separating the bins from each other.

18. The method of claim 1, wherein the method is performed for one or more other wafers, and wherein the set of bins generated for the wafer is not used as a set of bins for the one or more other wafers.

19. A non-transitory computer-readable medium, storing program instructions executable on a computer system for performing a computer-implemented method for generating a defect sample for a wafer, wherein the computer-implemented method comprises:

acquiring inspection results for the wafer, wherein the inspection results comprise information for defects detected on the wafer by an inspection process, and wherein the information comprises information for at least a first set of one or more first attributes for the defects and a second set of one or more second attributes for the defects;

identifying values of the one or more first attributes having the most diversity in the values of the one or more first attributes;

generating a set of bins for the defects based on the identified values such that each of the bins corresponds to only a portion of the values and such that the values corresponding to the bins have diversity in the one or more first attributes, wherein generating the set of bins does not include sampling any of the defects, wherein diversification of the set of bins in the one or more first attributes is controlled by a number of the bins in the set, and wherein the number of the bins in the set is received from a user prior to the generating step;

separating the defects into the bins based on the values of the one or more first attributes corresponding to the defects, wherein separating the defects into the bins is not performed until after the set of bins have been generated;

selecting, from one of the bins, defects within the one of the bins based on diversity in values of the one or more second attributes;

repeating said selecting for at least one other of the bins; and creating a defect sample for the wafer comprising the defects selected from the one of the bins and the at least one other of the bins.

20. A system configured to generate a defect sample for a wafer, comprising:

an inspection subsystem configured to acquire inspection results for the water, wherein the inspection results comprise information for defects detected on the wafer by an inspection process, and wherein the information comprises information for at least a first set of one or more first attributes for the defects and a second set of one or more second attributes for the defects; and a computer subsystem configured for:

identifying values of the one or more first attributes having the most diversity in the values of the one or more first attributes;

generating a set of bins for the defects based on the identified values such that each of the bins corresponds to only a portion of the values and such that the values corresponding to the bins have diversity in the one or more first attributes, wherein generating the set of bins does not include sampling any of the defects, wherein diversification of the set of bins in the one or more first attributes is controlled by a number of the bins in the set, and wherein the number of the bins in the set is received from a user prior to the generating step;

separating the defects into the bins based on the values of the one or more first attributes corresponding to the defects, wherein separating the defects into the bins is not performed until after the set of bins have been generated;

selecting, from one of the bins, defects within the one of the bins based on diversity in values of the one or more second attributes;

repeating said selecting for at least one other of the bins; and creating a defect sample for the wafer comprising the defects selected from the one of the bins and the at least one other of the bins.

21. The system of claim 20, wherein the one or more first attributes comprise one or more attributes of background of the defects on the wafer.

22. The system of claim 20, wherein the one or more second attributes comprise one or more characteristics of a signal detected for the defects in the inspection process.

23. The system of claim 20, wherein the wafer as unknown defectivity.

24. The system of claim 20, wherein the one or more first attributes are selected by a user.

25. The system of claim 20, wherein the computer subsystem is further configured for determining one or more characteristics of the bins based on the defects separated into the bins, displaying the one or more characteristics to a user prior to said selecting, and requesting from the user a validation of the one or more characteristics.

26. The system of claim 20, wherein the computer subsystem is further configured for determining one or more characteristics of the defects selected from the bins, displaying the one or more characteristics to a user prior to said creating, and requesting from the user a validation of the one or more characteristics.

27. The system of claim 20, wherein the computer subsystem is further configured for determining a first characteristic of the bins based on the defects separated into the bins, determining a second characteristic of the defects selected from the bins, wherein the first characteristic is not the same as the second characteristic, displaying the first and second characteristics to a user prior to said creating, and requesting from the user a validation of the first and second characteristics.

28. The system of claim 20, wherein said selecting is performed based on the diversity such that the defects selected from the one of the bins have the most diversity in the values of the one or more second attributes.

29. The system of claim 20, wherein said selecting is performed based on the diversity and one or more sample biasing parameters.

30. The system of claim 20, wherein the computer subsystem is further configured for separately selecting, from the one of the bins, defects within the one of the bins based on diversity in values of one or more third attributes of the defects, wherein the computer subsystem is further configured for repeating said separately selecting for the at least one other of the bins, and wherein creating the defect sample comprises adding the defects separately selected from the one of the bins and the at least one other of the bins to the defect sample.

31. The system of claim 20, wherein the computer subsystem is further configured for generating a set of sub-bins for a bin from which the defects were selected based on the values of the one or more second attributes such that each of the sub-bins corresponds to only a portion of the values of the one or more second attributes and such that the values of the one or more second attributes corresponding to the sub-bins have diversity in the one or more second attributes.

32. The system of claim 31, wherein the computer subsystem is further configured for separately selecting, from one of the sub-bins, defects within the one of the sub-bins based on diversity in values of one or more third attributes of the defects, wherein the computer subsystem is further configured for repeating said separately selecting for at least one other of the sub-bins, and wherein creating the defect sample comprises adding the defects separately selected from the one of the sub-bins and the at least one other of the sub-bins to the defect sample.

33. The system of claim 20, wherein the same number of defects are selected from each of the bins from which defects are selected.

34. The system of claim 20, wherein said selecting is performed independently for each of the bins from which defects are selected.

35. The system of claim 20, wherein the computer subsystem is further configured for storing information for the bins into which the defects are separated as a bin attribute for each of the defects that is separated into a bin, and Wherein said selecting and said repeating are performed based on the bin attributes of the defects.

36. The system of claim 20, wherein the steps performed by the computer subsystem do not comprise tuning cutlines separating the bins from each other.

37. The system of claim 20, wherein the set of bins generated for the wafer is not used as a set of bins for one or more other wafers.

\* \* \* \* \*